United States Patent
Mahajan et al.

(10) Patent No.: US 6,717,033 B1
(45) Date of Patent: Apr. 6, 2004

(54) POLY ADP-RIBOSE POLYMERASE GENE AND ITS USES

(75) Inventors: Pramod Mahajan, Urbandale, IA (US); Zhuang Zuo, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/236,995

(22) Filed: Jan. 26, 1999

Related U.S. Application Data

(60) Provisional application No. 60/072,785, filed on Jan. 27, 1998.

(51) Int. Cl.⁷ ................................................. A01H 4/00
(52) U.S. Cl. .................... 800/278; 800/320.1; 435/194; 435/320.1
(58) Field of Search .............................. 435/191, 320.1, 435/69.1, 6, 325, 295; 800/278, 295, 320.1

(56) References Cited

FOREIGN PATENT DOCUMENTS

| | | |
|---|---|---|
| EP | 0 757 102 A1 | 2/1997 |
| WO | WO 97/06267 * | 2/1997 |

OTHER PUBLICATIONS

Ikejima et al., The Zinc Fingers of Human Poly(ADP–ribose) Polymerase Are Differentially Required for the Recognition of DNA Breaks and Nicks and the Consequent Enzyme Activation, The Journal of Biological Chemistry, 1990, pp. 21907–21913, vol. 265, No. 35, The American Society for Biochemistry and Molecular Biology, Inc.

Semionov et al., Inhibition of Poly(ADP–ribose) Polymerase Stimulates Extrachromosomal Homologous Recombination in Mouse Ltk–Fibroblasts, Nucleic Acids Research, 1999, pp. 4526–4531, vol. 27, No. 22, Oxford University Press.

Ueda et al., ADP–Ribosylation, Ann. Rev. Biochem., 1985, pp. 73–100, vol. 54, Annual Reviews Inc.

Ushiro et al., Purification and Characterization of Poly (ADP–Ribose) Synthetase from Human Placenta, The Journal of Biological Chemistry, Feb. 15, 1987, pp. 2352–2357, vol. 262, No. 5, The American Society of Biological Chemists, Inc.

Burtscher et al., Isolation of ADP–Ribosyltransferase by Affinity Chromatography, Analytical Biochemistry, 1986, pp. 285–290, vol. 152, Academic Press, Inc.

Kofler et al., Purification and Characterization of NAD⁺: ADP–Ribosyltransferase (Polymerizing) From *Dictyostelium Discoideum*, Biochem J., 1993, pp. 275–281, vol. 293, Great Britain.

Chen et al., Poly(ADP–ribose) Polymerase in Plant Nuclei, Eur. J. Biochem., Feb. 1994, pp. 135–154, vol. 224, England.

Wang et al., Mice Lacking ADPRT and Poly(DP–Ribosyl)ation Develop Normally But Are Susceptible to Skin Disease, Genes and Development, 1995, pp. 509–520, vol. 9, Cold Spring Harbor Laboratory Press.

Lepiniec et al., Characterization of an *Arabidopsis thaliana* cDNA Homologue to Animal Poly(ADP–Ribose) Polymerase, FEBS Letters, 1995, pp. 103–108, vol. 364, Federation of European Biochemical Societies.

Schreiber et al., A Dominant–Negative Mutant of Human Poly(ADP–ribose) Polymerase Affects Cell Recovery, Apoptosis, and Sister Chromatid Exchange Following DNA Damage, Proc. Natl. Acad. Sci. USA, May 1995, pp. 4753–4757, vol. 92, Cell Biology.

Heller et al., Inactivation of the Poly(ADP–ribose) Polymerase Gene Affects Oxygen Radical and Nitric Oxide Toxicity in Islet Cells, The Journal of Biological Chemistry, May 12, 1995, pp. 11176–11180, vol. 270, No. 19, The American Society for Biochemistry and Molecular Biology, Inc.

Shah et al., Review: Methods for Biochemical Study of Poly(ADP–Ribose) Metabolism in Vitro and in Vivo, Analytical Biochemistry, 1995, pp. 1–13, vol. 227, Academic Press, Inc.

* cited by examiner

*Primary Examiner*—James Ketter
(74) *Attorney, Agent, or Firm*—Alston & Bird LLP

(57) ABSTRACT

Compositions and methods for influencing the metabolic state of plant cells are provided. The compositions comprise poly ADP-ribose polymerase genes and portions thereof, particularly the maize poly ADP-ribose polymerase gene as well as antisense nucleotide sequences for poly ADP-ribose polymerase genes. The nucleotide sequences find use in transforming plant cells to alter the metabolic state of the transformed plants and plant cells.

22 Claims, No Drawings

POLY ADP-RIBOSE POLYMERASE GENE AND ITS USES

CROSS-REFERENCE

This application claims the benefit of U.S. Provisional Application No. 60/072,785, filed Jan. 27, 1998.

FIELD OF THE INVENTION

The invention is drawn to the genetic manipulation of plants.

BACKGROUND OF THE INVENTION

The physiological and metabolic state of plant cells directly influences the plant response to external stimuli. The plant response to disease includes a host of cellular processes to enable plants to defend themselves from pathogenic agents. These processes apparently form an integrated set of resistance mechanisms that is activated by initial infection and then limits further spread of the invading pathogenic microorganism.

The transformation of plants is a complex process. The process involves contacting cells with a DNA to be integrated into the plant cell genome. Generally, genetic transformation of eukaryotic cells is a random event. That is, the foreign DNA is integrated into the genome at random positions. Often several copies, or parts of copies, of the transforming DNA are integrated in a single position, and/or at different positions, resulting in a transformed cell containing multiple copies of the foreign DNA.

Because the metabolic state of the plant cell is instrumental in various processes, it would be beneficial to be able to influence the state of the cells. Accordingly, there is a need for genes and methods for altering the metabolic state of plant cells.

SUMMARY OF THE INVENTION

Compositions and methods for influencing the metabolic state of plant cells are provided. The compositions comprise poly ADP-ribose polymerase genes and fragments thereof, particularly the maize poly ADP-ribose polymerase gene. The genes or antisense constructions of the genes can be used to transform plant cells and alter the metabolic state of the transformed cell.

In this manner, transformed plants can be obtained having altered metabolic states. The invention has implications in enhancing disease resistance in plants and for methods of genetic transformation of plants.

DETAILED DESCRIPTION OF THE INVENTION

Poly ADP-Ribose Polymerase genes and methods for their use are provided. In particular, the amino acid and nucleotide sequences for the maize poly ADP-ribose polymerase (PARP) are provided as SEQ ID NOs. 2 and 1, respectively. Also of interest are portions of the sequences of the invention. The nucleotide and amino acid sequences of the C-terminal domain of the maize poly ADP-ribose polymerase is provided in SEQ ID NOs. 3 and 4, respectively. The nucleotide sequence of the Zinc fingers is provided in SEQ ID NO. 5.

PARP is generally described as a nuclear enzyme found in most eukaryotes. Structure-function studies have shown that animal PARPs may be divided into at least three subdomains. The N-terminal part contains two zinc fingers and has a high affinity for nicked V-shaped DNA. Interaction of PARP with nicked DNA strongly enhances the activity of the catalytic domain, which is very well conserved among PARPs and located in the carboxyl-terminus of the protein. (Ueda et al. (1985) *Ann. Rev. Biochem.* 54:73–100; Sdhah et al. (1995) *Anal. Biochem.* 227:1–13).

PARP catalyzes both the transfer of ADP-ribose from $NAD^+$, mainly to the carboxyl group of a glutamic acid residue on target proteins, and subsequent ADP-ribose polymerization. (Ueda et al. (1985) *Ann. Rev. Biochem.* 54:73–100; Sdhah et al. (1995) *Anal. Biochem.* 227:1–13)

PARP is generally required in most cases where DNA is cleaved and rejoined, such as in DNA repair, DNA recombination, gene rearrangements and transposition. PARP has been shown to modify PARP itself, histones, high mobility group chromosomal proteins, topoisomerase, endonucleases and DNA polymerases. (Ueda et al. (1985) *Ann. Rev. Biochem.* 54:73–100; Sdhah et al. (1995) *Anal. Biochem.* 227:1–13).

Initially, the enzyme synthesizes an ester linkage preferentially between the glutamyl(-) or sometimes the C-terminal(-)carboxyl group on the acceptor protein and the 1'-OH of the ribosyly group of ADP-ribose. Subsequently, up to 45–50 ADP units are added via a 2'-1'phosphodiester bond. Branching of the poly (ADP)-ribosyl chains via the 2'-1'phosphodiester linkages is also observed. See, for example, Ueda et al. (1985) *Ann. Rev. Biochem.* 54:73–100; and Shah et al. (1995) *Anal. Biochem.* 227:1–13.

Compositions of the invention include isolated nucleic acid molecules encoding the PARP proteins of the invention, as well as fragments and variants thereof. The term "isolated" refers to material, such as a nucleic acid or a protein, which is: (1) substantially or essentially free from components that normally accompany or interact with it as found in its naturally occurring environment. Thus, for a nucleic acid, the sequence is lacking a flanking sequence either 3' or 5' or both. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by non-natural, synthetic (i.e., "man-made") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The nucleotide sequences of the invention can be used to isolate other homologous sequences in other plant species. Methods are readily available in the art for the hybridization of nucleic acid sequences. Coding sequences from other plants may be isolated according to well known techniques based on their sequence homology to the coding sequences set forth herein. In these techniques all or part of the maize coding sequence is used as a probe which selectively hybridizes to other PARP coding sequences present in a population of cloned genomic DNA fragments or cDNA fragments (i.e. genomic or cDNA libraries) from a chosen organism. For example, the entire maize PARP sequence or portions thereof may be used as probes capable of specifically hybridizing to corresponding coding sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify the PARP coding sequences of interest from a chosen organism by the well-known process of polymerase chain reaction (PCR). This technique may be used to isolate additional coding sequences from a desired organism or as a diagnostic assay to determine the presence of coding sequences in an organism.

Such techniques include hybridization screening of plated DNA libraries (either plaques or colonies; see, e.g., Sambrook et al., *Molecular Cloning*, eds., Cold Spring Harbor Laboratory Press (1989)) and amplification by PCR using oligonucleotide primers corresponding to sequence domains conserved among the amino acid sequences (see, e.g. Innis et al., *PCR Protocols, a Guide to Methods and Applications*, eds., Academic Press (1990)). For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37 C.; conditions represented by a wash stringency of 40–45% Formamide with 5×Denhardt's solution, 0.5% SDS, and 1×SSPE at 42 C.; and conditions represented by a wash stringency of 50% Formamide with 5×Denhardt's solution, 0.5% SDS and 1×SSPE at 42 C., respectively), to DNA encoding the PARP genes disclosed herein in a standard hybridization assay. See J. Sambrook et al., *Molecular Cloning, A Laboratory Manual 2d ed.* (1989) Cold Spring Harbor Laboratory. In general, sequences which code for the defense activators and other activator proteins of the invention and hybridize to the sequences disclosed herein will be at least 50% homologous, 70% homologous, and even 85% homologous or more with the disclosed sequence. That is, the sequence similarity of sequences may range, sharing at least about 50%, about 70%, and even about 85% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith et al. (1981) *Adv. Appl. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins et al. (1988) *Gene* 73:237–244; Higgins et al. (1989) *CABIOS* 5:151–153; Corpet et al. (1988) *Nucleic Acids Research* 16:10881–90; Huang et al. (1992) *Computer Applications in the Biosciences* 8:155–65, and Person et al. (1994) *Methods of Molecular Biology* 24:307–331; preferred computer alignment methods also include the BLASTP, BLASTN, and BLASTX algorithms. Altschul et al. (1990) *J. Mol. Biol.* 215:403–410. Alignment is also often performed by inspection and manual alignment.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. When sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid sequences for these purposes normally means sequence identity of at least 60%, more preferably at least 70%, 80%, 90%, and most preferably at least 95%. Polypeptides which are "substantially similar" share sequences as noted above except that residue positions which are not identical may differ by conservative amino acid changes.

Another indication that nucleotide sequences are substantially identical is if two molecules hybridize to each other under stringent conditions. Generally, stringent conditions are selected to be about 5 C. to about 20 C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60 C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) J. Mol. Biol. 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence confer resistance to nematodes. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the proteins of the invention.

By "variants" is intended substantially similar sequences. For nucleotide sequences, conservative variants include those sequences that, because of the degeneracy of the genetic code, encode the amino acid sequence of one of the proteins conferring resistance to nematodes. Generally, nucleotide sequence variants of the invention will have at least 70%, generally, 80%, preferably up to 90% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

The proteins of the invention may be altered in various ways including amino acid substitutions, deletions, truncations, and insertions. Methods for such manipulations are generally known in the art. For example, amino acid sequence variants of the activator proteins can be prepared by mutations in the DNA. Methods for mutagenesis and nucleotide sequence alterations are well known in the art. See, for example, Kunkel et al. (1985) Proc. Natl. Acad. Sci. USA 82:488–492; Kunkel et al. (1987) Methods in Enzymol. 154:367–382; U.S. Pat. No. 4,873,192; Walker and Gaastra (eds.) Techniques in Molecular Biology, MacMillan Publishing Company, NY (1983) and the references cited therein. Thus, the genes and nucleotide sequences of the invention include both the naturally occurring sequences as well as variant and mutant forms. Likewise, the proteins of the invention encompass both naturally occurring proteins as well as variants and modified forms thereof. Such variants will continue to possess the desired PARP activity. Obviously, the mutations that will be made in the DNA encoding the variant must not place the sequence out of reading frame and preferably will not create complementary regions that could produce secondary mRNA structure. See, EP Patent Application Publication No. 75,444.

PARP is present in all higher eukaryotes. Therefore, it is recognized that the nucleotide sequence encoding the PARP may be utilized from any eukaryotic source, including vertebrates, arthropods, mollusks, slime moulds, dinoflagellates, fungi, mammals, chicken, Xenopus and insects. See, for example, Heller et al. (1995) *J. Biol. Chem.* 270:11178–11180; Schreiber et al. (1995) *Proc. Natl. Acad. Sci. USA* 92:4753–4757; Ueda et al. (1985) *Ann. Rev. Biochem.* 54:73–100; Brightwell et al. (1975) *Biochem. J.* 147:119–129; Kofler et al. (1993) *ibid* 293:275–281; Collinge et al. (1994) *Mol. Gen. Genet.* 245:686–693; Scovassi et al. (1986) *Eur. J. Biochem.* 159:77–84; Simonin et al. (1991) *Anal. Biochem.* 195:226–231; Masutani et al. (1994) *Eur. J. Biochem.* 220:607–614; herein incorporated by reference.

It is recognized that the plant cell can be transformed with a nucleotide sequence encoding PARP, a nucleotide sequence encoding a portion of PARP, preferably the C-terminal portion of PARP, as well as with a nucleotide sequence encoding the antisense sequence for the PARP gene, or portions thereof. In this manner, the level of expression of the PARP in the plant cell can be modulated, i.e., increased or decreased, respectively. Levels of expression of the sense or antisense sequence can be regulated by the promoter utilized to express the gene.

Promoters for the expression of genes in plant cells are known in the art. Promoters are available for constitutive, tissue specific, inducible, etc. Such promoters include, for example, 35S promoter, Meyer et al. (1997) *J. Gen. Virol.* 78:3147–3151; biotin carboxylase, Bas et al. (1997) *Plant Mol. Biol.* 35:539–550; oxidase, Lasserre et al. (1997) *Mol. Gen. Genet* 256:211–222; cab, Shiina et al. (1997) *Plant Physiol.* 115:477–483; phospholipase, Xu et al. (1997) *Plant Physiol.* 115:387–395; farnesyltransferase, Zhou et al. (1997) *Plant J.* 12:921–930; plastocyanin, Helliwell et al. (1997) *Plant J.* 12:499–506; CVMV promoter, Verdaquer et al. (1996) *Plant Mol. Biol.* 31:1129–1139; actin, An et al. (1996) *Plant J.* 10:107–121; heat shock, Prandl et al. (1996) *Plant Mol. Biol.* 31:157–162; ubiquitin, thionin, 35S, Holtorf et al. (1995) *Plant Mol. Biol.* 29:637–646; Callis et al. (1990) *J. Biol. Chem.* 265:12486–12493; histone, Atanossova et al. (1992) *Plant J.* 2:291–300; rol C, Fladung et al. (1993) *Plant Mol. Biol.* 23:749–757; histone, Brignon et al. (1993) *Plant J.* 4:445–457; Lepetit et al. (1992) *Mol. Gen. Genet.* 231:276–285.

As indicated, recent studies on the mechanism of PARP suggests involvement of the enzyme in regulation of DNA repair, recombination and replication. The enzyme is rapidly activated by DNA and exhibits a high affinity for naked single-stranded or double-stranded DNA. Any perturbation in the cellular morphology and/or physiology that causes a change in chromatin conformation generally results in a rapid increase in PARP activity. PARP is an important modulator of the fate of DNA introduced into a plant cell. Accordingly, plants transformed with either a sense or antisense PARP nucleotide sequence may be utilized to increase transformation frequency in plant cells. Therefore, the present invention provides for the regulation of the levels of PARP in the plant cell to determine its effect on plant transformation and gene targeting.

It is further recognized that because the enzyme plays a role in cellular stress, it may be beneficial to increase the levels of the enzyme to prevent plant disease or pathogen attack. In this manner, constitutive or inducible promoters may be utilized. Constitutive promoters include, for example, those disclosed in U.S. Pat. Nos. 5,608,149; 5,608, 144; 5,604,121; 5,569,597; 5,466,785; 5,399,680; 5,268, 463; 5,608,142; herein incorporated by reference. Inducible promoters are known in the art and include, for example, pathogen inducible promoters, such as promoters from pathogenesis-related proteins (PR proteins) which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *The Plant Cell* 4:645–656; and Van Loon (1985) *Plant Mol. Virol.* 4:111–116. Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Molecular and General Genetics* 2:93–98; and Yang, Y (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen *Fusarium moniliforme* (see, for example, Cordero et al. (1992) *Physiological and Molecular Plant Pathology* 41:189–200).

The PARP genes or antisense nucleotides of the invention can be introduced into any plant. The genes or nucleotide sequences to be introduced will be used in expression cassettes for expression in any plant of interest.

Such expression cassettes will comprise a transcriptional initiation region linked to the gene encoding the PARP gene or antisense nucleotide of interest. Such an expression cassette is provided with a plurality of restriction sites for insertion of the gene of interest to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639.

The genes of the invention are provided in expression cassettes for expression in the plant of interest. The cassette will include 5' and 3' regulatory sequences operably linked to the gene of interest. The cassette may additionally contain at least one additional gene to be cotransformed into the organism. Alternatively, the additional gene(s) can be provided on another expression cassette. Where appropriate, the gene(s) may be optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94; untranslated leader from the coat protein mRNA of alfalfa mosaic virus (AMV RNA 4), (Jobling et al. (1987) *Nature* 325:622–625; tobacco mosaic virus leader (TMV), (Gallie, D. R. et al. (1989) *Molecular Biology of RNA*, pages 237–256; and maize chlorotic mottle virus leader (MCMV) (Lommel, S. A. et al. (1991) *Virology* 81:382–385). See also, Della-Cioppa et al. (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The genes of the present invention can be used to transform any plant. In this manner, genetically modified plants, plant cells, plant tissue, seed, and the like can be obtained. Transformation protocols may vary depending on the type of plant or plant cell, i.e. monocot or dicot, targeted for transformation. Suitable methods of transforming plant cells include microinjection (Crossway et al. (1986) *Biotechniques* 4:320–334), electroporation (Riggs et al. (1986) *Proc. Natl. Acad. Sci. USA* 83:5602–5606, Agrobacterium mediated transformation (Hinchee et al. (1988) *Biotechnology* 6:915–921), direct gene transfer (Paszkowski et al. (1984) *EMBO J.* 3:2717–2722), and ballistic particle acceleration (see, for example, Sanford et al., U.S. Pat. No. 4,945,050; Tomes et al. Direct DNA Transfer into Intact Plant Cells via Microprojectile Bombardment In Gamborg and Phillips (eds.) *Plant Cell, Tissue and Organ Culture: Fundamental Methods*, Springer-Verlag, Berlin (1995); and McCabe et al. (1988) *Biotechnology* 6:923–926). Also see, Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes et al. Direct DNA Transfer into Intact Plant Cells via Microprojectile Bombardment in Gamborg and Phillips (eds.) *Plant Cell, Tissue and Organ Culture: Fundamental Methods*, Springer-Verlag, Berlin (1995) (maize); Klein et al. (1988) *Plant Physiol.* 91:440–444 (maize); Fromm et al. (1990) *Biotechnology* 8:833–839 (maize); Hooydaas-Van Slogteren & Hooykaas (1984) *Nature (London)* 311:763–764; Bytebier et al. (1987) *Proc. Natl. Acad. Sci. USA* 84:5345–5349 (Liliaceae); De Wet et al. (1985) in *The Experimental Manipulation of Ovule Tissues* ed. G. P. Chapman et al., pp. 197–209. Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); D Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells which have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The present invention also provides isolated nucleic acid comprising polynucleotides of sufficient length and complementarity to a gene to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be employed for use in sense or antisense suppression of a PARP gene in a host cell, tissue, or plant. See, *Tools to Determine the Function of Genes*, 1995 Proceedings of the Fiftieth Annual Corn and Sorghum Industry Research Conference, American Seed Trade Association, Washington, D.C., 1995. Additionally, non-translated 5 or 3 regions of the polynucleotides of the present invention can be used to modulate turnover of heterologous mRNAs and/or protein synthesis.

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual,* Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tx., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a PARP gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a PARP gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

EXPERIMENTAL

Materials and Methods

Chemicals and Reagents

All chemicals used in this study were of molecular biology grade. Trizma base (Tris(hydroxymethyl) aminomethane; abbreviated hereafter as Tris), N-2 hydroxy-ethyl-piperazine-N'-2-ethane sulfonic acid (Hepes), Ethylenediaminetetraacetic acid, sodium salt (EDTA), Magnesium chloride, Urea, were procured from Sigma Chemical Co. Analytical grade glycerol was obtained from Baxter. Dithiothreitol (DTT), PefablocSC, Pepstatin, Bestatin, all restriction enzymes, DNA and RNA purification kits as well as markers were purchased from Boehringer Mannheim. Immunodetection kits for Western blots, silver staining and Colloidal Coomassie Blue staining were from Novex. All radioactive chemicals were purchased from NEN-Dupont and NEN. Chromotopographic resins were purchased either from Sigma, BioRad or Pharmacia.

Cell Culture

The enzyme is isolated from a Hi II embryogenic callus cell line. Exponentially growing cultures of 612B4 cells were maintained in dark at 28° C. (Armstrong et al. (1992) *Theor. Appl. Genet.* 84:755–762). The cell suspensions are in MS medium supplemented with 2-4-dichlorophenoxyacetic acid (2.5 mg/l). Cultures are grown for a week on a gyroratatory shaker at 150 rpm and harvested by decantation. Routinely, 60–80 g of cells are obtained from 800–900 ml cultures grown in 12–14 flasks.

Cells are harvested by filtration and used to prepare whole cell extracts (WCE) form 612B4 cells using the Bionebulizer (Glas-Col, Terre Haute, Ind.). The process for WCE preparation is outlined in Schema 1. All operations were carried out at 4° C. or on ice unless mentioned otherwise.

Chromatography on Heparin-agarose: About 300 ml of Heparin-agarose (Sigma) was washed extensively with 20 mM Hepes-KOH pH 7.9, 0.1 mM EDTA, 20% glycerol (HGED buffer), packed into a 5.0×30 cm Econo column (Biorad) and connected to the Econo System (Biorad). The matrix was equilibrated with HGED+100 mM KCl. Three batches of crude WCE extract (approx. 1.8–2.0 g of total pooled protein in 60–80 ml) were loaded on the column at a flow rate of 15–20 ml/hr. The column was washed extensively with equilibration buffer till the $A_{280}$ of the effluent was<0.1 unit (approx. 900 ml).

Small aliquots of peak fractions were saved for PARP assays and all fractions (7–8 ml each) showing $A_{280}$>0.1 unit were pooled. Protein was precipitated by adding solid ammonium sulfate (0.4 g/ml). The mixture was centrifuged at 40,000×g for 30 min., dissolved in minimum amount HGED and dialyzed against HGED+100 mM KCl containing Pefabloc and DTT. This fraction is designated HA-1. The column was further washed with 900 ml each HGED+ 400 mM KCl followed by HGED+1 M KCl. Fractions from both washes were processed as above and designated as HA-2 and HA-3. PARP assays were performed on HA-1, 2 and 3 and the active fraction (HA-2) was used for further purification.

Chromatography on DNA-cellulose: DNA-cellulose (Sigma) was washed extensively with HGED and packed in the Econo column (2.5×30 cm). The column was connected to the Econo System and equilibrated with HGED+100 mM KCI. Partially pure PARP from three Heparin-agarose column was loaded on the DNA-cellulose column. Unbound protein was removed by washing with HGED+100 mM KCI (200 ml; designated as DC-1). The bound protein was eluted with HGED+1M KCI (designated DC-2). All fractions was processed as described above for activity and protein.

Chromatography on Histone-agarose: Histone-agarose (Sigma) was washed extensively with HGED and packed into an Econo column (1.5×15 cm). The column was equilibrated in HGED+100 mM KCI. Active fraction from DNA-cellulose (DC-2) was further fractionated on Histone-agarose by washing the column successively with HGED containing 100 mM, 400 mM and 1 M KCI. All fractions were processed as above and dialyzed against 20 mM Tris-HCI buffer pH 7.9 containing 100 mM KCI.

Chromatography on Mini-Q column: Mini-Q column (Pharmacia) was connected to Smart-LC (Pharmacia) and equilibrated by washing with five bed volumes of HGED followed by five bed volumes of Tris-HCI buffer+100 mM KCI. Active PARP from the Histone-agarose step was loaded on the column. The column was washed with three bed volumes of equilibration buffer and 400 $\mu$l fractions were collected. Column was further developed using a step gradient of KCI at 400 mM, 600 mM and 1M in Tris-HCI, pH 8.0. All fractions were tested for PARP activity as described below.

Enzyme Assays

Catalytic activity of PARP is assayed following published protocols (Shah et al. (1995) Anal. Biochem 227:1–13) with modifications suitable for the plant enzyme. Briefly, the enzyme (in a total volume of 25 $\mu$l of 20 mM Hepes pH 7.9, 100 mM KCI) is incubated with 2.5–5 $\mu$Ci of $\infty$-$^{32}$P-NAD+, 2 $\mu$l/ml final concentration of bovine histone (fraction IV), 2 $\mu$g of activated calf thymus DNA and 0.5 mM DTT. The reactions are carried out at 6° C. unless otherwise mentioned. At the end of the appropriate time intervals, the labeled protein is precipitated with 25% TCA. The precipitate is collected by centrifugation at 16,000×g for 10 min., washed 2× with 5% TCA and counted in a LSC. Protein heated at 65° C. for 5 min. is used as a negative control.

Microsequencing

Protein samples obtained from the Mini-Q column purification step was electrophoresed in duplicate on a 10% polyacrylamide gels using 0.1% SDS in the running buffer (Shah et al. (1995) Anal. Biochem 227:1–13). One half of the gel was used to detect protein bands with a Colloidal Coormassie staining kit (Novex) following manufacturer s instructions. The other half was used in the activity blot assay to confirm position of the active PARP on the gel. Stained protein band corresponding to active PARP was cut out from the gel and used microsequencing carried out at the W. M. Keck Foundation Biotechnology Resource Laboratory if Yale University. In gel tryptic digestion of the protein, Matrix Assisted Laser Desorption Mass Spectrometry (MALDI-MS) of the isolated peptides, and amino sequencing of representative peptides was carried out following protocols detailed elsewhere (Stone et al. (1990) In: Methods in Enzyomology 193:389–412); (Stone et al. (1991) In: Methods in Protein Sequence Anal.ysis 133–141); Williams et al. (1995) In: Techniques in Protein Chemistry 6:143–152); Williams et al. (1995) In: Protein Protocol Handbook 365–378).

Antipeptide Antibodies

Synthesis of the peptide antigens and antibody generation was carried out at Research Genetics, Inc. Two peptides (P-1 and P-2) were used as for antibody generation using two different protocols. In the first protocol, peptide P-1 was synthesized as a multiple antigenic peptide (MAP) following published protocols (Tam, J. P. (1988) Proc. Nat. Acad. Sci. USA 85:5409–5413). Antiserum was collected and analyzed for cross-reactivity to PARP using Western blots (Shah et al. (1995) Anal. Biochem 227:1–13). In the second protocol, P-2 was synthesized as MAP (Tam, J. P. (1988) Proc. Natl. Acad. Sci. USA 85:5409–5413) as well as a linear peptide (Barany et al. (1980) In: The Peptides 2:1–284). The linear peptide was conjugated to hemocyanin using published methods (Walter et al. (1980) Proc. Natl. Acad. Sci. USA 77:5197–5200) and used for immunization. The immunization protocol for both types of antigens was essentially the same and is detailed below.

Two New Zealand rabbits (4–6 months old) were used for immunization with each type of antigen. The antigens were prepared by dissolving 500 $\mu$g MAP peptide in 500 $\mu$l of saline and mixed with equal 500 $\mu$l of complete Freund's adjuvant and injected subcutaneously at three to four dorsal sites. Same concentration of each antigen (in saline) was mixed with equal volume of incomplete Freund's adjuvant and injected as before at two, four and six weeks after the first immunization. Animals were bled from the auricular artery to collect 30–50 ml blood on days 0, 27, 57 and 69. Blood samples were allowed to clot at room temperature for 15 min. and serum was isolated from each sample by centrifugation at 5,000×g for 10 min. Cell-free serum was decanted gently into a clean tube and stored at −20° C. till further use.

cDNA Cloning

Total RNA was isolated from corn tissues with TRIzol Reagent (Life Technology, Inc. Gaithersburg, Md.) using a modification of the guanidine isothiocyanate/acid-phenol procedure described by Chomczynski and Sacchi (Chomczynski et al. (1987) Anal. Biochem 162:156). In brief, plant tissue samples were pulverized in liquid nitrogen before the addition of the TRIzol Reagent, and then were further homogenized with a mortar and pestle. Addition of chloroform by centrifugation was conducted for separation of an aqueous phase and an organic phase. The total RNA was recovered by precipitation with isopropyl alcohol from the aqueous phase.

The selection of poly(A)+RNA from total RNA was performed using PolyATract system (Promega Corporation, Madison, Wis.). In brief, biotinylated oligo (dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

Synthesis of the cDNA was performed and unidirectional cDNA libraries were constructed using the SuperScript Plasmid System (Life Technology, Inc., Gaithersburg, Md.). First strand of cDNA was synthesized by priming an oligo (dT) primer containing a Not I site. The reaction was catalyzed by SuperScript Reverse Transcriptase II at 45° C. The second strand of cDNA was labeled with alpha-$^{32}$P-dCTP and portions of the molecules smaller than 500 base pairs and unligated adapters were removed by Sephacryl-S400 chromatography. The selected cDNA molecules were ligated into pSPORT1 reference vector between the Not I and Sal I sites.

Individual colonies were picked and DNA was prepared either by PCR with M13 forward primers and M13 reverse primers, or by plasmid miniprep isolation. All the cDNA clones were sequenced using M13 reverse primers.

Analytical

Protein was estimated by the Bradford method (Bradford, M. (1976) *ibid* 72:248–254) using bovine γ-globulin as standard. Activity blots, Western blots and product analysis were performed essentially following published protocols (10, 20–22), except that all essays were carried out at 6° C.

Identification of Zinc Fingers

Two PCR primers were designed to encompass both the Zinc fingers of the maize PARP sequence. These primers were used for reverse transcriptase assisted PCR using the Titan 1 tube RT-PCR kit from Boeheringer Mannheim. Maize callus and leaf mRNA was used as template. The PCR product was purified using Qia Quick PCR product purification columns (Qiagen) and sequenced using an ABI sequencer. Sequenced data is shown in SEQ ID NO. 5.

Isolation of PARP from maize cells

Scheme I

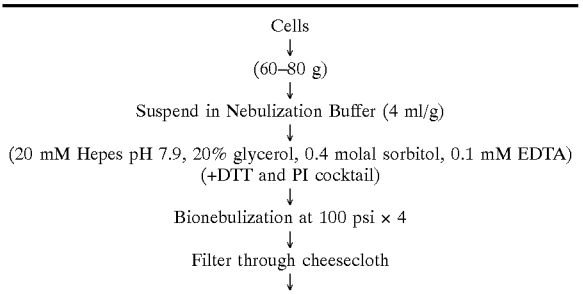

Isolation of PARP from maize cells

Scheme I

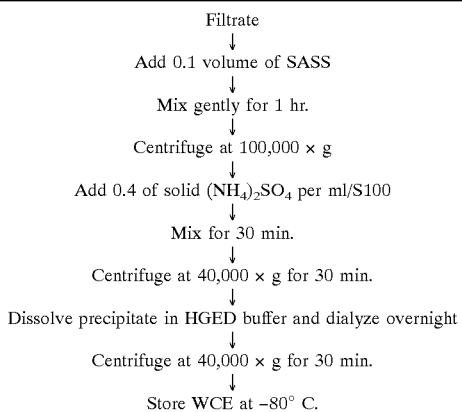

ll publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. An isolated DNA molecule comprising a nucleotide sequence selected from the group consisting of:

a) a nucleotide sequence encoding a poly ADP-ribose polymerase having the amino acid sequence set forth in SEQ ID NO. 2;

b) the nucleotide sequence set forth in SEQ ID NO. 1; and c) a nucleotide sequence that is antisense to the full-length sequence set forth in SEQ ID NO. 1.

2. A chimeric nucleic acid sequence comprising a promoter capable of driving expression of a nucleic acid in a platlet cell operably linked to a nucleotide sequence of claim 1.

3. The chimeric nucleic acid sequence of claim 2, wherein the nucleotide sequence encodes a poly ADP-ribose polymerase having the amino acid sequence set forth in SEQ ID NO. 2.

4. The chimeric nucleic acid sequence of claim 3, wherein said nucleotide sequence is the nucleotide sequence set forth in SEQ ID NO. 1.

5. A vector comprising the chimeric nucleic acid sequence of claim 4.

6. A plant cell transformed with the chimeric nucleic acid sequence of claim 4.

7. A transformed plant comprising the chimeric nucleic acid sequence of claim 4.

8. The chimeric nucleic acid sequence of claim 2, wherein the nucleotide sequence is antisense to the full-length sequence set forth in SEQ ID NO.1.

9. A vector comprising the chimeric nucleic acid sequence of claim 8.

10. A plant cell transformed with the vector of claim 9.

11. A transformed plant comprising the chimeric nucleic acid sequence of claim 8.

12. A transformed plant having incorporated into its genome a DNA molecule, said molecule comprising a promoter capable of driving expression of a nucleic acid sequence in a plant cell operably linked to a nucleotide sequence selected from the group consisting of:

a) a nucleotide sequence encoding a poly ADP-ribose polymerase having the amino acid sequence set forth in SEQ ID NO. 2;

b) the nucleotide sequence set forth in SEQ ID NO. 1; and c) a nucleotide sequence that is antisense to the full-length sequence set forth in SEQ ID NO. 1.

13. The transformed plant of claim 12, wherein the nucleotide sequence encodes a poly ADP-ribose polymerase having the amino acid sequence set forth in SEQ ID NO. 2.

14. The transformed plant or claim 13, wherein said coding sequence is the nucleotide sequence set forth in SEQ ID NO. 1.

15. The transformed plant of claim 12, wherein the nucleotide sequence is antisense to the full-length sequence set forth in SEQ ID NO. 1.

16. The transformed plant of claim 12, wherein said plant is a dicot.

17. The transformed plant of claim 12, wherein said plant is a monocot.

18. The transformed plant of claim 17, wherein said plant is maize.

19. Seed of the plant of any one of claims 16–18.

20. A method for modulating the metabolic state of a plant cell, said method comprising transforming said plant with a DNA construct, said construct comprising a promoter that drives expression in a plant cell operably linked with a nucleotide sequence selected from the group consisting of:

a) a nucleotide sequence encoding a poly ADP-ribose polymerase having the amino acid sequence set forth in SEQ ID NO. 2;

b) the nucleotide sequence set forth in SEQ ID NO. 1; and c) a nucleotide sequence that is antisense to the full-length sequence set forth in SEQ ID NO. 1.

21. The method of claim 20, wherein the nucleotide sequence encodes a poly ADP-ribose polymerase having the amino acid sequence set forth in SEQ ID NO. 2.

22. The method of claim 21, wherein said coding sequence is the nucleotide sequence set forth in SEQ ID NO. 1.

* * * * *

UNITED STATES PATENT AND TRADEMARK OFFICE
CERTIFICATE OF CORRECTION

PATENT NO.     : 6,717,033 B1
DATED          : April 6, 2004
INVENTOR(S)    : Mahajan et al.

It is certified that error appears in the above-identified patent and that said Letters Patent is hereby corrected as shown below:

<u>Title page,</u>
Item [56], References Cited, OTHER PUBLICATIONS, add the following:
-- Amor et al., *The Involvement of Poly(ADP-ribose) Polymerase in the Oxidative Stress Responses in Plants*, FEBS Letters, 1998, pp.1-7, Vol. 440, Federation of European Biochemical Societies.;
Babiychuk et al., *Zea mays mRNA for Poly(ADP-ribose) Polymerase 321bp*, EMBL Accession No. AJ222589, November 19, 1997;
Babiychuk et al., *Higher Plants Possess Two Structurally Different Poly(ADP-ribose) Polymerases*, The Plant Journal, 1998, pp. 635-645, Vol. 15(5), Blackwell Science Ltd.;
Girod et al., *Secondary Metabolism is Cultured Red Beet (Beta vulgaris L.) Cells: Differential Regulation of Betaxanthin and Betacyanin Biosynthesis*, Plant Cell Tissue Organ Cult, 1991, pp. 1-12, Vol. 25(1), Lab. Phyogene_que Cell, Lausanne, Switzerland.;
Küpper et al., *Molecular Genetic Systems to Study the Role of Poly(ADP-ribosyl)ation in the Cellular Response to DNA Damage*, Biochimie, 1995, pp. 450-455. Vol. 77.;
Lepiniec et al., *A. thaliana PARP mRNA for PARP Protein*, EMBL Accession No. Z48243, May 31, 1995.;
Lepiniec et al., *Characterization of an Arabidopsis thaliana cDNA Homologue to Animal Poly(ADP-ribose) Polymerase*, FEBS Letters, 1995, pp. 103-108, Vol. 364, Federation of European Biochemical Societies.;

UNITED STATES PATENT AND TRADEMARK OFFICE
CERTIFICATE OF CORRECTION

PATENT NO. : 6,717,033 B1
DATED : April 6, 2004
INVENTOR(S) : Mahajan et al.

It is certified that error appears in the above-identified patent and that said Letters Patent is hereby corrected as shown below:

Title page (cont'd),

Mahajan et al., *Purification and cDNA Cloning of Maize Poly(ADP)-Ribose Polymerase*, Plant Physiol., 1998, pp. 895-905, Vol. 118;

Mahajan et al., *Zea mays Poly(ADP)-Ribose Polymerase (PARP1) mRNA, Complete CDS*, EMBL Accession No. AF093627, November 30, 1998.;

Simbulan-Rosenthal et al., *Depletion of Nuclear Poly(ADP-ribose) Polymerase by Antisense RNA Expression: Influence on Genomic Stability, Chromatin Organization, DNA Repair, and DNA Replication*, Prog. Nucleic Acid Res. Mol. Biol., 1996, pp. 135-156, Vol. 55, Chemical Abstracts, Columbus, Ohio, USA;

Simbulan-Rosenthal et al., *The Expression of Poly(ADP-ribose) Polymerase During Differentiation-Linked DNA Replication Reveals That it is a Component of the Multiprotein DNA Replication Complex*, Biochemistry, 1996, pp. 11622-11633, Vol. 35, American Chemical Society.--

Column 31,
Line 6, "platelet" should read -- plant --.

Signed and Sealed this

First Day of March, 2005

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 2949
<212> TYPE: DNA
<213> ORGANISM: Zea mays
<220> FEATURE:
<221> NAME/KEY: CDS
<222> LOCATION: (1)...(2949)
<221> NAME/KEY: misc_feature
<222> LOCATION: 1584, 1588, 2078, 2107
<223> OTHER INFORMATION: n = A,T,C or G

<400> SEQUENCE: 1 atg gcg gcg ccg cca aag gcg tgg aag gcg gag tat gcc aag tct ggg      48
Met Ala Ala Pro Pro Lys Ala Trp Lys Ala Glu Tyr Ala Lys Ser Gly
 1               5                  10                  15 cgg gcc tcg tgc aag tca tgc cgg tcc cct atc gcc aag gac cag ctc      96
Arg Ala Ser Cys Lys Ser Cys Arg Ser Pro Ile Ala Lys Asp Gln Leu
            20                  25                  30 cgt ctt ggc aag atg gtt cag gcg tca cag ttc gac ggc ttc atg ccg     144
Arg Leu Gly Lys Met Val Gln Ala Ser Gln Phe Asp Gly Phe Met Pro
        35                  40                  45 atg tgg aac cat gcc agg tgc atc ttc agc aag aag aac cag ata aaa     192
Met Trp Asn His Ala Arg Cys Ile Phe Ser Lys Lys Asn Gln Ile Lys
```

-continued

| | | |
|---|---|---|
| tcc gtt gac gat gtt gaa ggg ata gat gca ctt aga tgg gat gat caa<br>Ser Val Asp Asp Val Glu Gly Ile Asp Ala Leu Arg Trp Asp Asp Gln<br>65                        70                       75                     80 | 240 |
| gag aag ata cga aac tac gtt ggg agt gcc tca gct ggt aca agt tct<br>Glu Lys Ile Arg Asn Tyr Val Gly Ser Ala Ser Ala Gly Thr Ser Ser<br>                     85                       90                     95 | 288 |
| aca gct gct cct cct gag aaa tgt aca att gag att gct cca tct gcc<br>Thr Ala Ala Pro Pro Glu Lys Cys Thr Ile Glu Ile Ala Pro Ser Ala<br>                   100                    105                 110 | 336 |
| cgt act tca tgt aga cga tgc agt gaa aag att aca aaa gga tcg gtc<br>Arg Thr Ser Cys Arg Arg Cys Ser Glu Lys Ile Thr Lys Gly Ser Val<br>           115                    120                    125 | 384 |
| cgt ctt tca gct aag ctt gag agt gaa ggt ccc aag ggt ata cca tgg<br>Arg Leu Ser Ala Lys Leu Glu Ser Glu Gly Pro Lys Gly Ile Pro Trp<br>130                     135                    140 | 432 |
| tat cat gcc aac tgt ttc ttt gag gta tcc ccg tct gca act gtt gag<br>Tyr His Ala Asn Cys Phe Phe Glu Val Ser Pro Ser Ala Thr Val Glu<br>145                     150                    155                 160 | 480 |
| aag ttc tca ggc tgg gat act ttg tcc gat gag gat aag aga acc atg<br>Lys Phe Ser Gly Trp Asp Thr Leu Ser Asp Glu Asp Lys Arg Thr Met<br>                   165                    170                 175 | 528 |
| ctc gat ctt gtt aaa aaa gat gtt ggc aac aat gaa caa aat aag ggt<br>Leu Asp Leu Val Lys Lys Asp Val Gly Asn Asn Glu Gln Asn Lys Gly<br>           180                    185                    190 | 576 |
| tcc aag cgc aag aaa agt gaa aat gat att gat agc tac aaa tcc gcc<br>Ser Lys Arg Lys Lys Ser Glu Asn Asp Ile Asp Ser Tyr Lys Ser Ala<br>           195                    200                    205 | 624 |
| agg tta gat gaa agt aca tct gaa ggt aca gtg cga aac aaa ggg caa<br>Arg Leu Asp Glu Ser Thr Ser Glu Gly Thr Val Arg Asn Lys Gly Gln<br>210                     215                    220 | 672 |
| ctt gta gac cca cgt ggt tcc aat act agt tca gct gat atc caa cta<br>Leu Val Asp Pro Arg Gly Ser Asn Thr Ser Ser Ala Asp Ile Gln Leu<br>225                     230                    235                 240 | 720 |
| aag ctt aag gag caa agt gac aca ctt tgg aag tta aag gat gga ctt<br>Lys Leu Lys Glu Gln Ser Asp Thr Leu Trp Lys Leu Lys Asp Gly Leu<br>                   245                    250                 255 | 768 |
| aag act cat gta tcg gct gct gaa tta agg gat atg ctt gag gct aat<br>Lys Thr His Val Ser Ala Ala Glu Leu Arg Asp Met Leu Glu Ala Asn<br>           260                    265                 270 | 816 |
| ggg cag gat aca tca gga cca gaa agg cac cta ttg gat cgc tgt gcg<br>Gly Gln Asp Thr Ser Gly Pro Glu Arg His Leu Leu Asp Arg Cys Ala<br>           275                    280                 285 | 864 |
| gat gga atg cta ttt gga gcg ctg ggt cct tgc cca gtc tgt gct aat<br>Asp Gly Met Leu Phe Gly Ala Leu Gly Pro Cys Pro Val Cys Ala Asn<br>           290                    295                 300 | 912 |
| ggc atg tac tat tat aat ggt cag tac caa tgc agt ggt aat gtg tca<br>Gly Met Tyr Tyr Tyr Asn Gly Gln Tyr Gln Cys Ser Gly Asn Val Ser<br>305                     310                    315                 320 | 960 |
| gag tgg tcc aag tgt aca tac tct gcc aca gaa cct gtc cgc gtt aag<br>Glu Trp Ser Lys Cys Thr Tyr Ser Ala Thr Glu Pro Val Arg Val Lys<br>                   325                    330                 335 | 1008 |
| aag aag tgg caa att cca cat gga aca aag aat gat tac ctt atg aag<br>Lys Lys Trp Gln Ile Pro His Gly Thr Lys Asn Asp Tyr Leu Met Lys<br>           340                    345                 350 | 1056 |
| tgg ttc aaa tct caa aag gtt aag aaa cca gag agg gtt ctt cca cca<br>Trp Phe Lys Ser Gln Lys Val Lys Lys Pro Glu Arg Val Leu Pro Pro<br>           355                    360                 365 | 1104 |
| atg tca cct gag aaa tct gga agt aaa gca act cag aga aca tca ttg | 1152 |

```
Met Ser Pro Glu Lys Ser Gly Ser Lys Ala Thr Gln Arg Thr Ser Leu
    370             375             380 ctg tct tct aaa ggg ttg gat aaa tta agg ttt tct gtt gta gga caa        1200
Leu Ser Ser Lys Gly Leu Asp Lys Leu Arg Phe Ser Val Val Gly Gln
385             390             395             400 tca aaa gaa gca gca aat gag tgg att gag aag ctc aaa ctt gct ggt        1248
Ser Lys Glu Ala Ala Asn Glu Trp Ile Glu Lys Leu Lys Leu Ala Gly
            405             410             415 gcc aac ttc tat gcc agg gtt gtc aaa gat att gat tgt tta att gca        1296
Ala Asn Phe Tyr Ala Arg Val Val Lys Asp Ile Asp Cys Leu Ile Ala
        420             425             430 tgt ggt gag ctc gac aat gaa aat gct gaa gtc agg aaa gca agg agg        1344
Cys Gly Glu Leu Asp Asn Glu Asn Ala Glu Val Arg Lys Ala Arg Arg
        435             440             445 ctg aag ata cca att gta agg gag ggt tac att gga gaa tgt gtt aaa        1392
Leu Lys Ile Pro Ile Val Arg Glu Gly Tyr Ile Gly Glu Cys Val Lys
    450             455             460 aga aca aaa tgc tgc cat ttg att tgt ata aac tgg aat gcc tta gag        1440
Arg Thr Lys Cys Cys His Leu Ile Cys Ile Asn Trp Asn Ala Leu Glu
465             470             475             480 tcc tca aaa ggc mgt act gtc act gtt aaa gtt aag ggc cga agt gct        1488
Ser Ser Lys Gly Xaa Thr Val Thr Val Lys Val Lys Gly Arg Ser Ala
            485             490             495 tgt tca tya agt cct cyg gtt tgc aag aat act gct cac att cct tra        1536
Cys Ser Xaa Ser Pro Xaa Val Cys Lys Asn Thr Ala His Ile Pro Xaa
            500             505             510 gra tgg gaa aag cat ata caa tgc amc ctt aaa cat gtt ctg acc tgn        1584
Xaa Trp Glu Lys His Ile Gln Cys Xaa Leu Lys His Val Leu Thr Xaa
        515             520             525 cac nag gtg tgy aca ggc tac tat gta ctc cag atc att gaa cag gat        1632
His Xaa Val Cys Thr Gly Tyr Tyr Val Leu Gln Ile Ile Glu Gln Asp
    530             535             540 gat ggg tct gag tgc tac gta ttt cgt aag tgg gga cgg gtt ggg agt        1680
Asp Gly Ser Glu Cys Tyr Val Phe Arg Lys Trp Gly Arg Val Gly Ser
545             550             555             560 gag aaa att gga ggg caa aaa ctg gag gag atg tca aaa act gag gca        1728
Glu Lys Ile Gly Gly Gln Lys Leu Glu Glu Met Ser Lys Thr Glu Ala
            565             570             575 atc aag gaa ttc aaa aga tta ttt ctt gag aag act gga aac tca tgg        1776
Ile Lys Glu Phe Lys Arg Leu Phe Leu Glu Lys Thr Gly Asn Ser Trp
        580             585             590 gaa gct tgg gaa tgt aaa acc aat ttt cgg aag cag cct ggg aga ttt        1824
Glu Ala Trp Glu Cys Lys Thr Asn Phe Arg Lys Gln Pro Gly Arg Phe
        595             600             605 tac cca ctt gat gtt gat tat ggt gtt aag aaa gca cca aaa cgg aaa        1872
Tyr Pro Leu Asp Val Asp Tyr Gly Val Lys Lys Ala Pro Lys Arg Lys
610             615             620 gat atc agt gaa atg aaa agt tct ctt gct cct caa ttg cta gaa ctc        1920
Asp Ile Ser Glu Met Lys Ser Ser Leu Ala Pro Gln Leu Leu Glu Leu
625             630             635             640 atg aag atg ctt ttc aat gtg gag aca tat aga gct gct atg atg gaa        1968
Met Lys Met Leu Phe Asn Val Glu Thr Tyr Arg Ala Ala Met Met Glu
            645             650             655 ttt gaa awt aat atg tca gaa atg cct ctt ggg aag cta agc mag gra        2016
Phe Glu Xaa Asn Met Ser Glu Met Pro Leu Gly Lys Leu Ser Xaa Xaa
            660             665             670 aat att gag raa gga ttt gaa gca tta act krg rta cmg rat tta ttt        2064
Asn Ile Glu Xaa Gly Phe Glu Ala Leu Thr Xaa Xaa Xaa Xaa Leu Phe
            675             680             685
```

-continued

| | | |
|---|---|---|
| gaa gga cac cgc tna tca agc act ggc ttg ttr gag aaa gct naa ttg<br>Glu Gly His Arg Xaa Ser Ser Thr Gly Leu Xaa Glu Lys Ala Xaa Leu<br>690                     695                     700 | 2112 |
| ttg ytg sga gcm ats syt ttt tca ctc tta tcc ctt cta ttc atc ctc<br>Leu Xaa Xaa Xaa Xaa Phe Ser Leu Leu Ser Leu Leu Phe Ile Leu<br>705                710                    715                  720 | 2160 |
| ata tta tac ggg atg agg atg att tca tat tca aag gcg aaa atg ctt<br>Ile Leu Tyr Gly Met Arg Met Ile Ser Tyr Ser Lys Ala Lys Met Leu<br>                     725                    730                  735 | 2208 |
| gaa gct ctg cag gat att gaa att gct tca aag ata gtt ggc ttc gat<br>Glu Ala Leu Gln Asp Ile Glu Ile Ala Ser Lys Ile Val Gly Phe Asp<br>           740                    745                  750 | 2256 |
| agc gac agt gat gaa tct ctt gat gat aaa tat atg aaa ctt cac tgt<br>Ser Asp Ser Asp Glu Ser Leu Asp Asp Lys Tyr Met Lys Leu His Cys<br>755                     760                    765 | 2304 |
| gac atc acc ccg ctg gct cac gat agt gaa gat tac aag tta att gag<br>Asp Ile Thr Pro Leu Ala His Asp Ser Glu Asp Tyr Lys Leu Ile Glu<br>           770                    775                  780 | 2352 |
| cag tat ctc ctc aac aca cat gct cct act cac aag gac tgg tcg ctg<br>Gln Tyr Leu Leu Asn Thr His Ala Pro Thr His Lys Asp Trp Ser Leu<br>785                     790                    795                  800 | 2400 |
| gaa ctg gag gaa gtt ttt tca ctt gat cga gat gga gaa ctt aat aag<br>Glu Leu Glu Glu Val Phe Ser Leu Asp Arg Asp Gly Glu Leu Asn Lys<br>                        805                    810                  815 | 2448 |
| tac tca aga tat aaa aat aat ctg cat aac aag atg cta tta tgg cac<br>Tyr Ser Arg Tyr Lys Asn Asn Leu His Asn Lys Met Leu Leu Trp His<br>                820                    825                  830 | 2496 |
| ggt tca agg ttg acg aat ttt gtg gga att ctt agt caa ggg cta aga<br>Gly Ser Arg Leu Thr Asn Phe Val Gly Ile Leu Ser Gln Gly Leu Arg<br>835                     840                    845 | 2544 |
| att gca cct cct gag gca cct gtt act ggc tat atg ttc ggc aaa ggc<br>Ile Ala Pro Pro Glu Ala Pro Val Thr Gly Tyr Met Phe Gly Lys Gly<br>850                     855                    860 | 2592 |
| ctc tac ttt gca gat cta gta agc aag agc gca caa tac tgt tat gtg<br>Leu Tyr Phe Ala Asp Leu Val Ser Lys Ser Ala Gln Tyr Cys Tyr Val<br>865                     870                    875                  880 | 2640 |
| gat agg aat aat cct gta ggt ttg atg ctt ctt tct gag gtt gct tta<br>Asp Arg Asn Asn Pro Val Gly Leu Met Leu Leu Ser Glu Val Ala Leu<br>                     885                    890                  895 | 2688 |
| gga gac atg tat gaa cta aag aaa gcc acg tcc atg gac aaa cct cca<br>Gly Asp Met Tyr Glu Leu Lys Lys Ala Thr Ser Met Asp Lys Pro Pro<br>           900                    905                  910 | 2736 |
| aga ggg aag cat tcg acc aag gga tta ggc aaa acc gtg cca ctg gag<br>Arg Gly Lys His Ser Thr Lys Gly Leu Gly Lys Thr Val Pro Leu Glu<br>                915                    920                  925 | 2784 |
| tca gag ttt gtg aag tgg agg gat gat gtc gta gtt ccc tgc ggc aag<br>Ser Glu Phe Val Lys Trp Arg Asp Asp Val Val Val Pro Cys Gly Lys<br>930                     935                    940 | 2832 |
| ccg gtg cca tca tca att agg agc tct gaa ctc atg tac aat gag tac<br>Pro Val Pro Ser Ser Ile Arg Ser Ser Glu Leu Met Tyr Asn Glu Tyr<br>945                     950                    955                  960 | 2880 |
| atc gtc tac aac aca tcc cag gtg aag atg cag ttc ttg ctg aag gtg<br>Ile Val Tyr Asn Thr Ser Gln Val Lys Met Gln Phe Leu Leu Lys Val<br>                     965                    970                  975 | 2928 |
| cgt ttc cat cac aag agg tag<br>Arg Phe His His Lys Arg *<br>           980 | 2949 |

<210> SEQ ID NO 2
<211> LENGTH: 982

-continued

```
<212> TYPE: PRT
<213> ORGANISM: Zea mays
<220> FEATURE:
<221> NAME/KEY: VARIANT
<222> LOCATION: 485, 499, 502, 512, 513, 521, 528, 530, 659, 671, 672,
      676, 683, 684, 685, 686, 693, 699, 703, 706, 707, 708, 709, 710
<223> OTHER INFORMATION: Xaa = Any Amino Acid

<400> SEQUENCE: 2

Met Ala Ala Pro Pro Lys Ala Trp Lys Ala Glu Tyr Ala Lys Ser Gly
1               5                   10                  15

Arg Ala Ser Cys Lys Ser Cys Arg Ser Pro Ile Ala Lys Asp Gln Leu
            20                  25                  30

Arg Leu Gly Lys Met Val Gln Ala Ser Gln Phe Asp Gly Phe Met Pro
        35                  40                  45

Met Trp Asn His Ala Arg Cys Ile Phe Ser Lys Lys Asn Gln Ile Lys
50                  55                  60

Ser Val Asp Asp Val Glu Gly Ile Asp Ala Leu Arg Trp Asp Asp Gln
65                  70                  75                  80

Glu Lys Ile Arg Asn Tyr Val Gly Ser Ala Ser Ala Gly Thr Ser Ser
                85                  90                  95

Thr Ala Ala Pro Pro Glu Lys Cys Thr Ile Glu Ile Ala Pro Ser Ala
            100                 105                 110

Arg Thr Ser Cys Arg Arg Cys Ser Glu Lys Ile Thr Lys Gly Ser Val
        115                 120                 125

Arg Leu Ser Ala Lys Leu Glu Ser Glu Pro Lys Gly Ile Pro Trp
130                 135                 140

Tyr His Ala Asn Cys Phe Phe Glu Val Ser Pro Ser Ala Thr Val Glu
145                 150                 155                 160

Lys Phe Ser Gly Trp Asp Thr Leu Ser Asp Glu Asp Lys Arg Thr Met
            165                 170                 175

Leu Asp Leu Val Lys Lys Asp Val Gly Asn Asn Glu Gln Asn Lys Gly
        180                 185                 190

Ser Lys Arg Lys Lys Ser Glu Asn Asp Ile Asp Ser Tyr Lys Ser Ala
    195                 200                 205

Arg Leu Asp Glu Ser Thr Ser Glu Gly Thr Val Arg Asn Lys Gly Gln
210                 215                 220

Leu Val Asp Pro Arg Gly Ser Asn Thr Ser Ser Ala Asp Ile Gln Leu
225                 230                 235                 240

Lys Leu Lys Glu Gln Ser Asp Thr Leu Trp Lys Leu Lys Asp Gly Leu
            245                 250                 255

Lys Thr His Val Ser Ala Ala Glu Leu Arg Asp Met Leu Glu Ala Asn
        260                 265                 270

Gly Gln Asp Thr Ser Gly Pro Glu Arg His Leu Leu Asp Arg Cys Ala
    275                 280                 285

Asp Gly Met Leu Phe Gly Ala Leu Gly Pro Cys Pro Val Cys Ala Asn
290                 295                 300

Gly Met Tyr Tyr Tyr Asn Gly Tyr Gln Cys Ser Gly Asn Val Ser
305                 310                 315                 320

Glu Trp Ser Lys Cys Thr Tyr Ser Ala Thr Glu Pro Val Arg Val Lys
            325                 330                 335

Lys Lys Trp Gln Ile Pro His Gly Thr Lys Asn Asp Tyr Leu Met Lys
        340                 345                 350

Trp Phe Lys Ser Gln Lys Val Lys Pro Glu Arg Val Leu Pro Pro
    355                 360                 365
```

-continued

```
Met Ser Pro Glu Lys Ser Gly Ser Lys Ala Thr Gln Arg Thr Ser Leu
    370                 375                 380
Leu Ser Ser Lys Gly Leu Asp Lys Leu Arg Phe Ser Val Val Gly Gln
385                 390                 395                 400
Ser Lys Glu Ala Ala Asn Glu Trp Ile Glu Lys Leu Lys Leu Ala Gly
                405                 410                 415
Ala Asn Phe Tyr Ala Arg Val Val Lys Asp Ile Asp Cys Leu Ile Ala
            420                 425                 430
Cys Gly Glu Leu Asp Asn Glu Asn Ala Glu Val Arg Lys Ala Arg Arg
        435                 440                 445
Leu Lys Ile Pro Ile Val Arg Glu Gly Tyr Ile Gly Glu Cys Val Lys
    450                 455                 460
Arg Thr Lys Cys Cys His Leu Ile Cys Ile Asn Trp Asn Ala Leu Glu
465                 470                 475                 480
Ser Ser Lys Gly Xaa Thr Val Thr Val Lys Val Lys Gly Arg Ser Ala
                485                 490                 495
Cys Ser Xaa Ser Pro Xaa Val Cys Lys Asn Thr Ala His Ile Pro Xaa
            500                 505                 510
Xaa Trp Glu Lys His Ile Gln Cys Xaa Leu Lys His Val Leu Thr Xaa
        515                 520                 525
His Xaa Val Cys Thr Gly Tyr Tyr Val Leu Gln Ile Ile Glu Gln Asp
    530                 535                 540
Asp Gly Ser Glu Cys Tyr Val Phe Arg Lys Trp Gly Arg Val Gly Ser
545                 550                 555                 560
Glu Lys Ile Gly Gly Gln Lys Leu Glu Glu Met Ser Lys Thr Glu Ala
                565                 570                 575
Ile Lys Glu Phe Lys Arg Leu Phe Leu Glu Lys Thr Gly Asn Ser Trp
            580                 585                 590
Glu Ala Trp Glu Cys Lys Thr Asn Phe Arg Lys Gln Pro Gly Arg Phe
        595                 600                 605
Tyr Pro Leu Asp Val Asp Tyr Gly Val Lys Ala Pro Lys Arg Lys
    610                 615                 620
Asp Ile Ser Glu Met Lys Ser Ser Leu Ala Pro Gln Leu Leu Glu Leu
625                 630                 635                 640
Met Lys Met Leu Phe Asn Val Glu Thr Tyr Arg Ala Ala Met Met Glu
                645                 650                 655
Phe Glu Xaa Asn Met Ser Glu Met Pro Leu Gly Lys Leu Ser Xaa Xaa
            660                 665                 670
Asn Ile Glu Xaa Gly Phe Glu Ala Leu Thr Xaa Xaa Xaa Xaa Leu Phe
        675                 680                 685
Glu Gly His Arg Xaa Ser Ser Thr Gly Leu Xaa Glu Lys Ala Xaa Leu
    690                 695                 700
Leu Xaa Xaa Xaa Xaa Xaa Phe Ser Leu Leu Ser Leu Leu Phe Ile Leu
705                 710                 715                 720
Ile Leu Tyr Gly Met Arg Met Ile Ser Tyr Ser Lys Ala Lys Met Leu
                725                 730                 735
Glu Ala Leu Gln Asp Ile Glu Ile Ala Ser Lys Ile Val Gly Phe Asp
            740                 745                 750
Ser Asp Ser Asp Glu Ser Leu Asp Asp Lys Tyr Met Lys Leu His Cys
        755                 760                 765
Asp Ile Thr Pro Leu Ala His Asp Ser Glu Asp Tyr Lys Leu Ile Glu
    770                 775                 780
Gln Tyr Leu Leu Asn Thr His Ala Pro Thr His Lys Asp Trp Ser Leu
```

```
                                                                  785                  790                  795                  800
Glu Leu Glu Glu Val Phe Ser Leu Asp Arg Asp Gly Glu Leu Asn Lys
                    805                  810                  815

Tyr Ser Arg Tyr Lys Asn Asn Leu His Asn Lys Met Leu Leu Trp His
            820                  825                  830

Gly Ser Arg Leu Thr Asn Phe Val Gly Ile Leu Ser Gln Gly Leu Arg
            835                  840                  845

Ile Ala Pro Pro Glu Ala Pro Val Thr Gly Tyr Met Phe Gly Lys Gly
            850                  855                  860

Leu Tyr Phe Ala Asp Leu Val Ser Lys Ser Ala Gln Tyr Cys Tyr Val
865                  870                  875                  880

Asp Arg Asn Asn Pro Val Gly Leu Met Leu Leu Ser Glu Val Ala Leu
                    885                  890                  895

Gly Asp Met Tyr Glu Leu Lys Lys Ala Thr Ser Met Asp Lys Pro Pro
            900                  905                  910

Arg Gly Lys His Ser Thr Lys Gly Leu Gly Lys Thr Val Pro Leu Glu
            915                  920                  925

Ser Glu Phe Val Lys Trp Arg Asp Asp Val Val Pro Cys Gly Lys
    930                  935                  940

Pro Val Pro Ser Ser Ile Arg Ser Ser Glu Leu Met Tyr Asn Glu Tyr
945                  950                  955                  960

Ile Val Tyr Asn Thr Ser Gln Val Lys Met Gln Phe Leu Leu Lys Val
                    965                  970                  975

Arg Phe His His Lys Arg
            980

<210> SEQ ID NO 3
<211> LENGTH: 474
<212> TYPE: DNA
<213> ORGANISM: Zea mays
<220> FEATURE:
<221> NAME/KEY: CDS
<222> LOCATION: (1)...(474)

<400> SEQUENCE: 3 aac aag atg cta tta tgg cac ggt tca agg ttg acg aat ttt gtg gga      48
Asn Lys Met Leu Leu Trp His Gly Ser Arg Leu Thr Asn Phe Val Gly
 1               5                  10                  15 att ctt agt caa ggg cta aga att gca cct cct gag gca cct gtt act      96
Ile Leu Ser Gln Gly Leu Arg Ile Ala Pro Pro Glu Ala Pro Val Thr
                20                  25                  30 ggc tat atg ttc ggc aaa ggc ctc tac ttt gca gat cta gta agc aag     144
Gly Tyr Met Phe Gly Lys Gly Leu Tyr Phe Ala Asp Leu Val Ser Lys
            35                  40                  45 agc gca caa tac tgt tat gtg gat agg aat aat cct gta ggt ttg atg     192
Ser Ala Gln Tyr Cys Tyr Val Asp Arg Asn Asn Pro Val Gly Leu Met
     50                  55                  60 ctt ctt tct gag gtt gct tta gga gac atg tat gaa cta aag aaa gcc     240
Leu Leu Ser Glu Val Ala Leu Gly Asp Met Tyr Glu Leu Lys Lys Ala
 65                  70                  75                  80 acg tcc atg gac aaa cct cca aga ggg aag cat tcg acc aag gga tta     288
Thr Ser Met Asp Lys Pro Pro Arg Gly Lys His Ser Thr Lys Gly Leu
                 85                  90                  95 ggc aaa acc gtg cca ctg gag tca gag ttt gtg aag tgg agg gat gat     336
Gly Lys Thr Val Pro Leu Glu Ser Glu Phe Val Lys Trp Arg Asp Asp
            100                 105                 110 gtc gta gtt ccc tgc ggc aag ccg gtg cca tca tca att agg agc tct     384
Val Val Val Pro Cys Gly Lys Pro Val Pro Ser Ser Ile Arg Ser Ser
        115                 120                 125
```

-continued

```
                 115                 120                      125
gaa ctc atg tac aat gag tac atc gtc tac aac aca tcc cag gtg aag     432
Glu Leu Met Tyr Asn Glu Tyr Ile Val Tyr Asn Thr Ser Gln Val Lys
    130                 135                     140 atg cag ttc ttg ctg aag gtg cgt ttc cat cac aag agg tag             474
Met Gln Phe Leu Leu Lys Val Arg Phe His His Lys Arg  *
145                 150                 155
```

<210> SEQ ID NO 4
<211> LENGTH: 157
<212> TYPE: PRT
<213> ORGANISM: Zea mays

<400> SEQUENCE: 4

```
Asn Lys Met Leu Leu Trp His Gly Ser Arg Leu Thr Asn Phe Val Gly
1               5                   10                  15

Ile Leu Ser Gln Gly Leu Arg Ile Ala Pro Pro Glu Ala Pro Val Thr
                20                  25                  30

Gly Tyr Met Phe Gly Lys Gly Leu Tyr Phe Ala Asp Leu Val Ser Lys
            35                  40                  45

Ser Ala Gln Tyr Cys Tyr Val Asp Arg Asn Asn Pro Val Gly Leu Met
        50                  55                  60

Leu Leu Ser Glu Val Ala Leu Gly Asp Met Tyr Glu Leu Lys Lys Ala
65                  70                  75                  80

Thr Ser Met Asp Lys Pro Pro Arg Gly Lys His Ser Thr Lys Gly Leu
                85                  90                  95

Gly Lys Thr Val Pro Leu Glu Ser Glu Phe Val Lys Trp Arg Asp Asp
            100                 105                 110

Val Val Val Pro Cys Gly Lys Pro Val Pro Ser Ser Ile Arg Ser Ser
        115                 120                 125

Glu Leu Met Tyr Asn Glu Tyr Ile Val Tyr Asn Thr Ser Gln Val Lys
    130                 135                 140

Met Gln Phe Leu Leu Lys Val Arg Phe His His Lys Arg
145                 150                 155
```

<210> SEQ ID NO 5
<211> LENGTH: 530
<212> TYPE: DNA
<213> ORGANISM: Zea mays

<400> SEQUENCE: 5

```
ctcgtgcaag tcatgccggt cccctatcgc caaggaccag ctccgtcttg gcaagatggt    60
tcaggcgtca cagttcgacg gcttcatgcc gatgtggaac catgccaggt gcatcttcag   120
caagaagaac cagataaaat ccgttgacga tgttgaaggg atagatgcac ttagatggga   180
tgatcaagag aagatacgaa actacgttgg gagtgcctca gctggtacaa gttctacagc   240
tgctcctcct gagaaatgta caattgagat tgctccatct gcccgtactt catgtagacg   300
atgcagtgaa aagattacaa aaggatcggt ccgtctttca gctaagcttg agagtgaagg   360
tcccaagggt ataccatggt atcatgccaa ctgtttcttt gaggtatccc cgtctgcaac   420
tgttgagaag ttctcaggct gggatacttt gtccgatgag gataagagaa ccatgctcga   480
tcttgttaaa aaagatgttg gcaacaatga acaaaataag ggttccaagc               530
```